US007150981B2

(12) United States Patent
Habuchi et al.

(10) Patent No.: US 7,150,981 B2
(45) Date of Patent: Dec. 19, 2006

(54) SULFATE TRANSFERASE AND DNA ENCODING THIS ENZYME

(75) Inventors: Hiroko Habuchi, Nagoya (JP); Koji Kimata, Nagoya (JP)

(73) Assignee: Seikagaku Corporation, Tokyo (JP)

( * ) Notice: Subject to any disclaimer, the term of this patent is extended or adjusted under 35 U.S.C. 154(b) by 556 days.

(21) Appl. No.: 10/312,892

(22) PCT Filed: Jun. 29, 2001

(86) PCT No.: PCT/JP01/05673

§ 371 (c)(1),
(2), (4) Date: Dec. 30, 2002

(87) PCT Pub. No.: WO02/00889

PCT Pub. Date: Jan. 3, 2002

(65) Prior Publication Data

US 2004/0053253 A1 Mar. 18, 2004

(30) Foreign Application Priority Data

Jun. 29, 2000 (JP) ............................ 2000-197251

(51) Int. Cl.

| | |
|---|---|
| ***C12N 9/10*** | (2006.01) |
| ***C12N 9/00*** | (2006.01) |
| ***C12N 15/09*** | (2006.01) |
| ***C12Q 1/68*** | (2006.01) |
| ***C12P 21/68*** | (2006.01) |
| ***C08B 37/10*** | (2006.01) |

(52) U.S. Cl. .......................... 435/193; 435/183; 435/6; 435/69.1; 435/320.1

(58) Field of Classification Search ................ 435/193, 435/23.2; 536/23.2
See application file for complete search history.

(56) References Cited

FOREIGN PATENT DOCUMENTS

| | | | |
|---|---|---|---|
| EP | 967272 | A2 | 12/1999 |
| JP | 11-69983 | A | 3/1999 |
| JP | 2002-60566 | A | 2/2002 |
| WO | WO 01/90334 | A2 | 11/2001 |
| WO | WO 02/12467 | | 2/2002 |

OTHER PUBLICATIONS

Habuchi et al., EMBL Database Accession No. Q9QYK6, "Heparan sulfate 6-sulfotransferase 2", created May 1, 2000.*

Habuchi, H, et al., The Occurrence of Three Isoforms of Heparan Sulfate 6-O-Sulfotransferase Having Different Specificities for Hexuronic Acid Adjacent to the Targeted N-Sulfoglucosamine, J. Biol. Chem., Jan. 2000, vol. 275, pp. 2859-2868.

Supplementary Partial European Search Report completed on Mar. 24, 2004 and issued to a pending related application.

Supplementary European Search Report completed on Jul. 6, 2004 and issued to a related foreign application.

* cited by examiner

*Primary Examiner*—Rebecca E. Prouty
*Assistant Examiner*—Iqbal Chowdhury
(74) *Attorney, Agent, or Firm*—Knobbe, Martens, Olson & Bear LLP

(57) ABSTRACT

A glycosaminoglycan 6-O-sulfotransferase having an activity of transferring sulfate to a hydroxyl at position 6 of a glycosamine residue of a glycosaminoglycan, which has a ratio of relative activities to substrates satisfying completely desulfated N-acetylated (CDSNAc) heparin/completely desulfated N-resulfated (CDSNS) heparin≧0.05 and a molecular weight as calculated from constituent amino acids of from 53,000 to 58,000 daltons.

1 Claim, 3 Drawing Sheets

SULFATE TRANSFERASE AND DNA ENCODING THIS ENZYME

TECHNICAL FIELD

The present invention relates to a sulfotransferase and to DNA encoding it. More particularly, the present invention relates to a polypeptide of 6-O-sulfotransferase which selectively sulfates the hydroxyl at position 6 of a glucosamine residue contained in a glycosaminoglycan which is a sulfate acceptor, and to DNA encoding the polypeptide.

BACKGROUND ART

Heparin and heparan sulfate are glycosaminoglycans having a repeating unit (4GlcAβ1/IdoAα1→4GlcNAcα1→) composed of two sugars, i.e., a hexuronic acid (HexA) residue (D-glucuronic acid (GlcA) or L-iduronic acid (IdoA) residue) and an N-acetylglucosamine (GlcNAc) residue as a basic skeleton (heparin skeleton), basically with a portion of hydroxyl at position 2 of the hexuronic acid residues and a portion of amino groups at position 2 or hydroxyl at position 6 of the N-acetylglucosamine residue being replaced with sulfates.

Cloning of the gene of an enzyme which transfers sulfate to glycosaminoglycans (glycosaminoglycan sulfotransferase) has made it possible to readily obtain the enzyme in amounts sufficient enough to obtain information on the biosynthesis of glycosaminoglycans having sulfates (sulfated glycosaminoglycans). This will presumably provide a useful approach to investigation on the relationship between the structure and function of sulfated glycosaminoglycans. It has been known that the biosynthesis of sulfated glycosaminoglycans, in particular, biosynthesis of heparin and heparan sulfate, is achieved by a variety of sulfation processes (Kobata, H., Hakomori, S., Nagai, K., Glycotechnology (5), 57 (1994), published by Kodansha Scientific). This sulfation may involve various glycosaminoglycan sulfotransferases. As the glycosaminoglycan sulfotransferases which transfer sulfate to heparin or heparan sulfate, heparan sulfate N-sulfotransferase (hereinafter in some cases abbreviated as "HSNST") which catalyzes de-N-acetylation of N-acetylglucosamine residue and sulfate transfer; heparan sulfate 2-O-sulfotransferase (hereinafter in some cases abbreviated as "HS2ST") which transfers sulfate to hydroxyl at position 2 of hexuronic acid residue; and heparan sulfate 6-O-sulfotransferase (hereinafter in some cases abbreviated as "HS6ST") which transfers sulfate to hydroxyl at position 6 of N-sulfated glycosamine residue, have been isolated and for some of the sulfotransferases, cDNA cloning has already been performed.

The inventors of the present invention have already purified HS6ST which selectively transfers sulfate from 3'-phosphoadenosine 5'-phosphosulfate which is the sulphate donor, to hydroxyl at position 6 of N-sulfated glucosamine residue contained in heparan sulfate which is the sulfate acceptor, from cultured cells derived from Chinese hamster, mouse, and human (J. Biol. Chem., 270, 4172–4179 (1995)), have completed cloning of the enzyme (J. Biol. Chem., 273, 9208–9213 (1998)), and have succeeded in further cloning two of the isoforms in mouse (J. Biol. Chem., 275, 2859–2868 (2000)).

DISCLOSURE OF THE INVENTION

Known HS6ST which selectively transfers sulfate to a hydroxyl at position 6 of an N-sulfated glucosamine residue contained in heparan sulfate exhibits a strong enzymatic activity to CDSNS (completely desulfated N-resulfated) heparin but a very weak sulfate transfer activity to sugar chains having substantially no sulfate in amino groups in a glucosamine residue such as CDSNAc (completely desulfated N-acetylated) heparin, which limits modification of the heparin skeletal structure by using the enzyme. In order to obtain many types of modified forms, sulfotransferases having different substrate specificities are needed. Therefore, an object of the present invention is to provide novel glycosaminoglycan sulfotransferases which selectively sulfate hydroxyl at position 6 of a glucosamine residue of the heparin skeleton and which also exhibit sufficient activities to CDSNAc heparin.

The inventors of the present invention extensively searched corresponding DNAs of enzymes in humans from human cDNA based on the nucleotide sequence of DNA of one of isoforms of the above-mentioned HS6ST in mouse (hereinafter referred to as "mHS6ST2"). Surprisingly, the inventors have found that besides the corresponding human isoform having a high homology to mHS6ST2 (hereinafter referred to as "hHS6ST2"), another enzyme having a different substrate specificity to that of mHS6ST2 and having a homology to the hHS6ST2 is expressed and confirmed that this enzyme has different properties to those of known sulfotransferases, thereby achieving the present invention.

Thus, the present invention provides the followings:

(1) A glycosaminoglycan 6-O-sulfotransferase having an activity of transferring sulfate to a hydroxyl at position 6 of a glycosamine residue of a glycosaminoglycan, which has a ratio of relative activities to substrates satisfying Completely Desulfated N-Acetylated (CDSNAc) heparin/Completely Desulfated N-Sulfated (CDSNS) heparin $\geqq$0.05 and a molecular weight as calculated from constituent amino acids of from 53,000 to 58,000 daltons.

(2) A glycosaminoglycan 6-O-sulfotransferase having an activity of transferring sulfate to a hydroxyl at position 6 of a glycosamine residue of a glycosaminoglycan, which has a ratio of relative activities to substrates satisfying N-Sulfated (NS) heparosan/Completely Desulfated N-Sulfated (CDSNS) heparin $\geqq$1.90 and a molecular weight as calculated from constituent amino acids of from 53,000 to 58,000 daltons.

(3) A glycosaminoglycan 6-O-sulfotransferase having an activity of transferring sulfate to a hydroxyl at position 6 of a glycosamine residue of a glycosaminoglycan, which comprises a polypeptide having an amino acid sequence of SEQ ID NO: 2 or an amino acid sequence including substitution, deletion, insertion, or translocation of one or a few amino acids in the amino acid sequence of SEQ ID NO: 2.

(4) An enzyme according to the item (3), in which the polypeptide has a molecular weight of 53,000 to 58,000 daltons.

(5) An enzyme according to the item (3) or (4), in which the ratio of relative activities to substrates satisfies N-Sulfated (NS) heparosan/Completely Desulfated N-Sulfated (CDSNS) heparin $\geqq$1.90.

(6) A polypeptide of the following {1} or {2}:

{1} a polypeptide having an amino acid sequence of SEQ ID NO: 2; and

{2} a polypeptide having an amino acid sequence including substitution, deletion, insertion, or translocation of one or a few amino acids in the amino acid sequence of the polypeptide of {1} and having the same antigenicity as that of the polypeptide of {1} or having an enzymatic activity to transfer sulfate to hydroxyl at position 6 of a glycosamine residue in a glycosaminoglycan.

(7) A polypeptide having an amino acid sequence including substitution, deletion, insertion, or translocation of one or a few amino acids in the amino acid sequence of SEQ ID NO: 2, in which the polypeptide has an enzymatic activity to transfer sulfate to hydroxyl at position 6 of a glycosamine residue in a glycosaminoglycan and also has a ratio of relative activities to substrates satisfying N-Sulfated (NS) heparosan/Completely Desulfated N-Sulfated (CDSNS) heparin ≧1.90.

(8) A DNA encoding the polypeptide of the enzyme as defined in any one of the items (1) to (5) or the polypeptide as defined in the item (6) or (7).

(9) A DNA encoding a polypeptide of the following {1} or {2}:

{1} a polypeptide having an amino acid sequence of SEQ ID NO: 2; and

{2} a polypeptide having an amino acid sequence including substitution, deletion, insertion, or translocation of one or a few amino acids in the amino acid sequence of the polypeptide of {1} and having the same antigenicity as that of the polypeptide of {1} or having an enzymatic activity to transfer sulfate to hydroxyl at position 6 of a glycosamine residue in a glycosaminoglycan.

(10) A DNA of any one of the followings (a) to (d):

(a) a DNA having a nucleotide sequence of SEQ ID NO: 1;

(b) a DNA having a nucleotide sequence of nucleotide residues 2 to 1381 in SEQ ID NO: 1;

(c) a DNA having a nucleotide sequence which is complementary to the nucleotide sequence of the DNA of (a) or (b); and (d) a DNA which hybridizes with the DNA of (a), (b), or (c) under stringent conditions, the DNA encoding a polypeptide which has an enzymatic activity to transfer sulfate to hydroxyl at position 6 of a glycosamine residue in a glycosaminoglycan.

(11) A DNA according to the item (10), in which a polypeptide which the DNA encodes has a ratio of relative activities to substrates satisfying N-Sulfated (NS) heparosan/Completely Desulfated N-Sulfated (CDSNS) heparin ≧1.90.

(12) A recombinant vector comprising the DNA as defined in any one of the items (8) to (11).

(13) A transformant which is transformed with the recombinant vector as defined in the item (12).

(14) A method for producing the enzyme as defined in any one of the items (1) to (5), comprising culturing the transformant as defined in the item (13) and isolating the enzyme as defined in the item (1) or (2).

(15) A polypeptide of the following {3} or {4}:

{3} a polypeptide having an amino acid sequence of SEQ ID NO: 4; and

{4} a polypeptide having of an amino acid sequence including substitution, deletion, insertion, or translocation of one or a few amino acids in the amino acid sequence of the polypeptide described in {3} and having an enzymatic activity to transfer sulfate to hydroxyl at position 6 of a glycosamine residue in a glycosaminoglycan or having the same antigenicity as that of the polypeptide described in {3}.

(16) A DNA encoding a polypeptide of the following {3} or {4}:

{3} a polypeptide having an amino acid sequence of SEQ ID NO: 4; and

{4} a polypeptide having an amino acid sequence including substitution, deletion, insertion, or translocation of one or a few amino acids in the amino acid sequence of the polypeptide of {3} and having an enzymatic activity to transfer sulfate to hydroxyl at position 6 of a glycosamine residue in a glycosaminoglycan or having the same antigenicity as that of the polypeptide described in {3} above.

(17) A DNA of any one of (e) to (h):

(e) a DNA having a nucleotide sequence of SEQ ID NO: 3;

(f) a DNA consisting of a nucleotide sequence of nucleotide residues 15 to 1514 in SEQ ID NO: 3;

(g) a DNA having a nucleotide sequence which is complementary to the nucleotide sequence of the DNA of (e) or (f); and (h) a human-derived DNA which hybridizes with the DNA in (e), (f), or (g) above under stringent conditions.

(18) A method for detecting tumorigenesis of a tissue, comprising relating an expression amount of the polypeptide as defined in the item (6), (7), or (15) to presence of a tumor in the tissue.

(19) A method for detecting tumorigenesis of a tissue, comprising relating an expression amount of mRNA generated by transcription of the DNA as defined in the item (10) or (17) to presence of a tumor in the tissue.

BEST MODE FOR CARRYING OUT THE INVENTION

Figure 1:
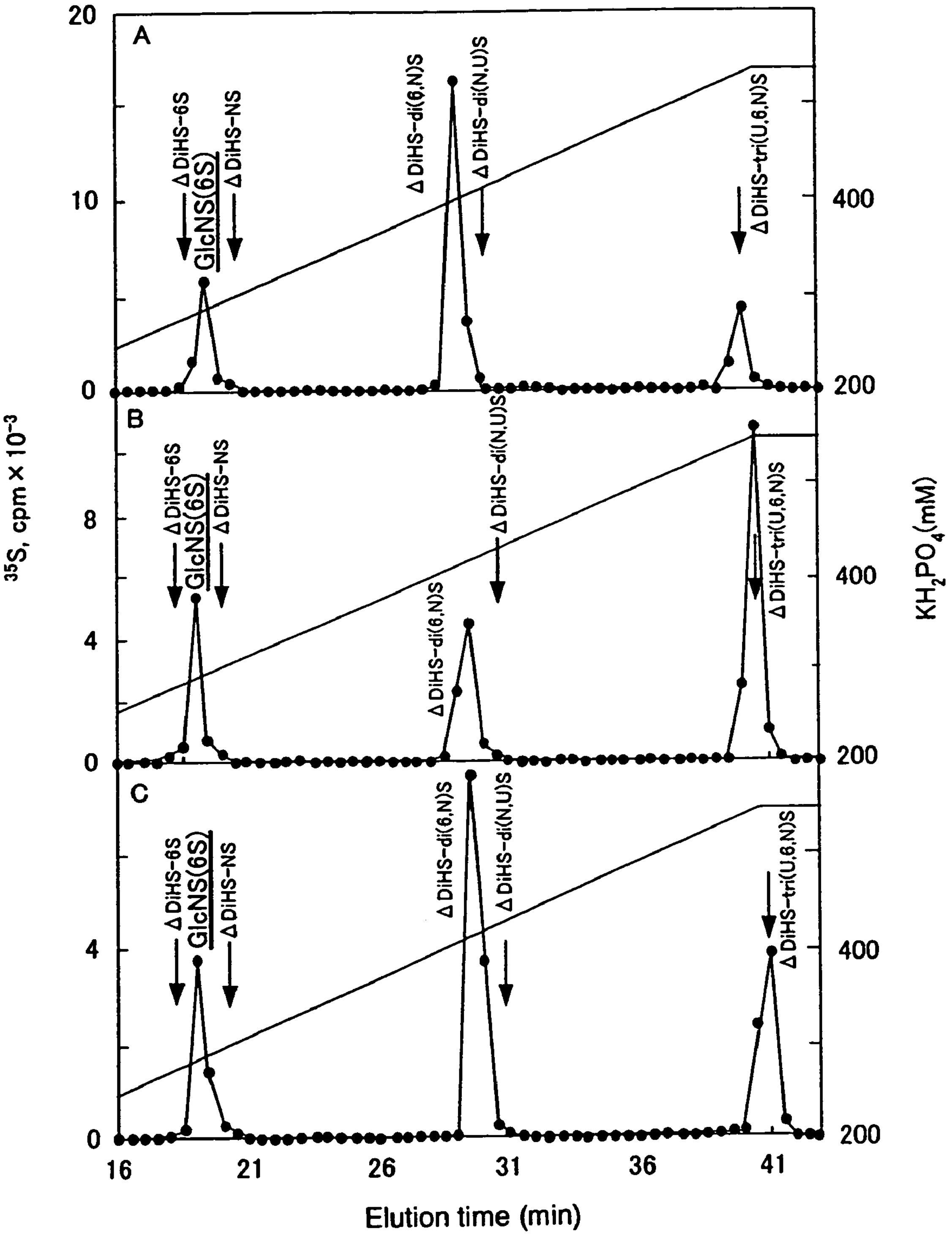
FIG. 1 shows results of digestion of heparan sulfates modified with human HS6ST isoforms, i.e., hHS6ST2, hHS6ST2v, and hHS6ST1, by heparin-degrading enzymes and fractionation by high performance liquid chromatography. A: hHS6ST1, B: hHS6ST2, C: hHS6ST2v.

Hereinafter, embodiments of the present invention are described.

<1>Enzyme of the Present Invention

The enzyme of the present invention is a glycosaminoglycan 6-O-sulfotransferase having an activity of transferring sulfate to a hydroxyl at position 6 of a glycosamine residue of a glycosaminoglycan, and has at least one of the followings properties (1) to (4):

(1) A ratio of relative activities to substrates satisfying Completely Desulfated N-Acetylated (CDSNAc) heparin/Completely Desulfated N-Sulfated (CDSNS) heparin ≧0.05;

(2) A molecular weight as calculated from constituent amino acids being from 53,000 to 58,000 daltons;

(3) A ratio of relative activities to substrates satisfying N-Sulfated (NS) heparosan/Completely Desulfated N-Sulfated (CDSNS) heparin ≧1.90; and (4) Its polypeptide having an amino acid sequence of SEQ ID NO: 2 or an amino acid sequence including substitution, deletion, insertion, or translocation of one or a few amino acids in the amino acid sequence of SEQ ID NO: 2.

The enzyme of the present invention usually has the following physical and chemical properties:

(1) Action:

It selectively transfers sulfate from a sulfate donor to hydroxyl at position 6 of a glucosamine residue contained in a sulfate acceptor.

(2) Substrate Specificity:

It transfers sulfate to hydroxyl at position 6 of a glucosamine residue in CDSNS heparin (Completely Desulfated, N-Sulfated Heparin), CDSNAC heparin (Completely Desulfated, N-Acetylated Heparin), N-Sulfated (NS) heparosan, and heparin, but it does not transfer sulfate to chondroitin sulfate A and chondroitin sulfate C. A sulfate transfer activity to NDSNAc heparin is not less than 5%, preferably not less than 6%, and more preferably not less than 7% based on that to CDSNS heparin. That is, a ratio of the sulfate transfer activity to CDSNAc heparin to the sulfate transfer activity to CDSNS heparin (CDSNAc heparin/CDSNS heparin) is not less than 0.05, preferably not less than 0.06, and more preferably not less than 0.07. Also, a sulfate transfer activity to NS heparosan is not less than 190%, and more preferably not less than 200% based on that to CDSNS heparin. That is, a ratio of the sulfate transfer activity to NS heparosan to the sulfate transfer activity to CDSNS heparin (NS heparosan/CDSNS heparin) is not less than 1.90 and preferably not less than 2.00.

(3) Molecular Weight:

Calculated amount of the molecular weight of the polypeptide which constitutes the enzyme (value calculated from the amino acid sequence) is 53,000 Da or more and 58,000 Da or less.

The physical and chemical properties described above can be measured according to the method described in J. Biol. Chem. 270, 4172–4179 (1995).

Although the enzyme of the present invention may be derived from any mammalian so far as it has the above-mentioned properties, it is particularly preferred that the enzyme is derived from human.

The sulfate donor for the enzyme of the present invention preferably includes active sulfate (3'-phosphoadenosine 5'-phosphate; hereinafter also referred to as "PAPS").

For the enzyme of the present invention, an enzyme whose polypeptide has an amino acid sequence of SEQ ID NO: 2 is preferable. However, if the polypeptide of an enzyme has an amino acid sequence including substitution, deletion, insertion, or translocation of one or a few amino acids in the amino acid sequence of SEQ ID NO: 2, such an enzyme is also encompassed by the enzyme of the present invention so far as the enzyme having a polypeptide having such an amino acid sequence has at least the action described in (1) above and the substrate specificity. The word "a few" in respect of amino acids in the above-mentioned polypeptide refers to a number corresponding to 10% or less of the number of amino acids constituting the polypeptide.

One skilled in the art can easily select substitution, deletion, insertion, or translocation of one amino or more acids which will give substantially no damage to the enzyme activity by confirming whether or not the targeted enzyme activity is present according to the above-mentioned measuring method for the activity.

Preferably, the enzyme of the present invention further has the following properties. That is, a sulfate transfer activity to the hydroxyl at position 6 of a glucosamine residue in heparan sulfate derived from mouse EHS tumor, when measured by the activity measuring method described in Examples hereinbelow, is 1.0 or more time, preferably 1.05 or more times, and particularly preferably 1.3 or more times that to CDSNS heparin. On the other hand, the enzyme of the present invention transfers substantially no sulfate to hexuronic acid.

<2> DNA1 of the Present Invention and Polypeptide Encoded by the Same

The DNA1 of the present invention is a DNA which encodes the polypeptide of the enzyme of the present invention described in <1> above.

Specific examples of the DNA1 of the present invention include a DNA having a nucleotide sequence encoding the entire amino acid sequence of SEQ ID NO: 2, which is the polypeptide hHS6ST2v, and DNA having a nucleotide sequence encoding a polypeptide having an amino acid sequence of SEQ ID NO: 2 including substitution, deletion, insertion, or translocation of one or a few amino acids and having the same antigenicity as that of the polypeptide having the amino acid sequence of SEQ ID NO: 2 or having an enzyme activity to transfer sulfate to the hydroxyl at position 6 of a glucosamine residue contained in a glycosaminoglycan with CDSNAc heparin/CDSNS heparin being not less than 0.05, and preferably not less than 0.06. A DNA having a nucleotide sequence encoding a polypeptide whose CDSNAc heparin/CDSNS heparin is not less than 0.07 is most preferred. However, the present invention is not limited thereto.

Also, the DNA1 of the present invention is a DNA having a nucleotide sequence encoding a polypeptide whose NS heparosan/CDSNS heparin is preferably not less than 1.90, and more preferably not less than 2.00.

That is, such a DNA is not limited so far as an enzyme containing the polypeptide encoded by the DNA has the above-mentioned physical and chemical properties of the enzyme of the present invention. Specific examples of such a DNA include a DNA having the nucleotide sequence of SEQ ID NO: 1, a DNA having a nucleotide sequence of nucleotide residues 2 to 1381 (coding region) of the nucleotide sequence of SEQ ID NO: 1, and a DNA which hybridizes with these DNAs under stringent conditions. Further examples of the DNA1 of the present invention include DNAs and RNAs having nucleotide sequences complementary to DNAs having the above-mentioned exemplary nucleotide sequences. Furthermore, DNAs may be either single stranded or double stranded. DNAs are not limited so far as they have the above-mentioned nucleotide sequences or nucleotide sequences complementary thereto. Also, the DNA1 of the present invention may contain the sequence of an intron which is to be removed before translation.

As the stringent conditions described above, conditions in which 50% formaldehyde, 5×SSPE (sodium chloride/sodium phosphate/EDTA (ethylenediaminetetraacetic acid) buffer), 5× Denhardt's solution, 0.5% SDS (sodium dodecylsulfate), and 100 μg/ml of denatured salmon sperm are present at 42° C. and conditions substantially the same as these are exemplified. That is, the stringent conditions are conditions which are used in usual hybridization of genes. Those conditions used in a Northern blotting method, a Southern blotting method, screening using hybridization of nucleic acids, etc. are included in the "stringent conditions" as used herein.

Substitution, deletion, insertion, or translocation of nucleotide or nucleotides in the nucleotide sequence of the DNA which causes the above-mentioned substitution, deletion, insertion, or translocation of one amino or more acids in an amino acid sequence can be introduced into a DNA, for example, by synthesizing a sequence with both ends thereof being cleaved with a restriction enzyme and containing both sides of the mutation site therein, and replacing the corresponding portion of the nucleotide sequence in a non-mutated DNA. Also, substitution, deletion, insertion, or translocation of nucleotide or nucleotides may be introduced into DNA by a site specific mutation (Kremer, W. and Frits, H. J., Meth. In Enzymol., 154, 350 (1987); Kunkel, T. A. et al., Meth. In Enzymol., 154, 367 (1987)) and the like.

Note that one skilled in the art can readily understand that DNAs having different nucleotide sequences due to degeneracy of genetic codes are also included in the DNA1 of the present invention.

Preferably, the DNA1 of the present invention has a nucleotide sequence having 95% or more homology as calculated using a gene analysis computer program GENETYX-MAC (manufactured by Software Development Co., Ltd.) to the nucleotide sequence of nucleotide residues 2 to 1381 of the nucleotide sequence of SEQ ID NO: 1.

The DNA1 of the present invention is preferably DNA which is expressed mainly in at least one of testis, ovary, and kidney as well as in brain and which is further expressed in pancreas and pituitary gland in a slight amount.

<3> Preparation Method for DNA1 of the Present Invention

The DNA1 of the present invention can be prepared by amplification by a PCR (Polymerase Chain Reaction) method or the like from cDNA by using primers prepared based on the nucleotide sequence of mHS6ST2 or that of human EST or the like corresponding thereto. It can also be prepared by artificial synthesis based on the nucleotide sequence of the DNA1 of the present invention disclosed by the present invention. Also, one skilled in the art can prepare the DNA1 of the present invention from a cDNA library or total RNA of human origin by artificially preparing primers based on the nucleotide sequence of the DNA1 of the present invention and using the primers. Furthermore, by using the above-mentioned primers, a DNA encoding a corresponding enzyme present in a mammalian other than humans can be obtained from a cDNA library or total RNA of the other mammalian origin.

In particular, the DNA1 of the present invention can be produced by cloning comprising the following steps:

(1) preparation of primers by using mouse HS6ST2 and human EST (Expression Sequence Tag);

(2) amplification of cDNA by a PCR method using the primers prepared in (1) above; and (3) recovery and cloning of the PCR product.

Usually, the full-length cDNA of the present invention is selected by screening.

However, the production method for the DNA1 of the present invention is not limited to this and the DNA1 of the present invention can be produced by the above-mentioned PCR method as well as other known cDNA cloning technique.

Hereinafter, one example of the production method for DNA of the present invention using cDNA of HS6ST2 of mouse origin (mHS6ST2) (J. Biol. Chem., 275, 2859–2868 (2000)) will be specifically described.

(1) Preparation of Primers by Using Mouse HS6ST2 (mHS6ST2) and Human EST

Preparation of primers for PCR may be performed in the same manner as in ordinary methods. However, it is preferred that a nucleotide sequence of DNA of human origin be used for preparing the primer for amplifying cDNA of human HS6ST2v. Therefore, it is preferred to search for a corresponding human EST from an EST database by using cDNA of mHS6ST2 and prepare a primer based on the sequence of the human EST. Examples of such an EST that can be used for the preparation of primers include one recorded in dbEST of GenBank under register No. AL049679. 5' Primer and 3' primer do not have to be prepared based on the nucleotide sequence of human DNA. For example, one of them may be prepared based on the nuleotide sequence of cDNA of mHS6ST2 and the other may be prepared based on the nucleotide sequence of human EST. Examples of such primers include primers having nucleotide sequences of SEQ ID NO: 5 and SEQ ID NO: 6.

(2) Amplification of cDNA by a PCR Method

By using the above-prepared primers, cDNA prepared from cells is amplified by a PCR method.

cDNA can be prepared by a conventional method. Also, a commercially available cDNA library may also be used. cDNA can be prepared, for example, by the following method.

That is, total RNA can be obtained from cultured cells or cells collected from a tissue by, for example, a guanidine thiocyanate/CsCl method (Kngston, R. S., (1991) in Current Protocols in Molecular Biology, Suppl. 14, Unit 4.2, Green Publishing Associates and Wiley Interscience, New York) or the like. The material is not particularly limited so far as it expresses mRNA of HS6ST2v.

From the total RNA thus obtained, poly(A)$^+$RNA is purified by oligo dT (Oligo-(dT)) cellulose column chromatography or the like and further a reverse transcription PCR method by using a random oligo nucleotide primer is performed allowing preparation of cDNA.

It is also preferred to use commercially available cDNA as the above-mentioned cDNA in consideration of ease of operation.

Amplification of the cDNA described above by a PCR method using the above-mentioned primers results in specific amplification of the cDNA of HS6ST2v. The PCR method can be performed by, for example, the method as described below.

That is, 3 μl of an aqueous solution containing a cDNA library is heated at 95° C. for 3 minutes and then immediately ice-cooled to denature cDNA. To the denatured cDNA, distilled water is added and left to stand at 0° C. for 20 minutes or more and then the above-mentioned primers are added. To the mixture, a reverse transcription reaction mixture, four kinds of deoxynucleotide triphosphates, and AmpliTaq polymerase are added. The amplification reaction, which is composed of, for example, denaturation reaction at 94° C. for 30 seconds, annealing at 55° C. for 30 seconds, and elongation reaction at 72° C. for 2 minutes, is repeatedly performed 35 times. Thereafter, a further 15 minutes of elongation reaction is carried out. However, the conditions of the PCR method, such as the number of repetition and temperature, may be adjusted appropriately.

In addition, preparation of cDNA is conveniently performed with a commercially available cDNA synthesis kit. Examples of such a kit include Taq PCR Core Kit (manufactured by Qiagen, K.K.). Also, use of, for example, TimeSaver cDNA synthesis kit (manufactured by Pharmacia LKB Biotechnology, AB) allows coupling of cDNA to cloning vector as well as synthesis of cDNA.

Analysis of DNA amplified by such methods by separation means according to molecular weight, for example, agarose gel electrophoresis reveals amplification of HS6ST2v (about 1,360 bp) and HS6ST2 (about 1,500 bp).

(3) Recovery and Cloning of PCR Product

Among cDNAs amplified by the PCR method, the PCR product of about 1,360 bp is recovered by a conventional method. For example, where the PCR product is fractionated by gel electrophoresis according to molecular weight, a method of taking out DNA from gel, such as Jetsorb may be used.

The recovered PCR product is ligated with a restriction enzyme region and this is inserted to a cloning vector to introduce (transfect) it into a host bacterium cell by a conventional method.

The host bacterium cell to be used must be selected by a cloning vector to be used. Usually, a combination of a cloning vector whose host is *Escherichia coli* (*E. coli*) and *E. coli* is frequently used. However, the present invention is not limited to this. Transfection is performed usually by mixing with *E. coli* of which the permeability of its cell membrane has been changed in the presence of recombinant DNA and 30 mM calcium chloride. In the case of λ phage vector such as λgt11, recombinant DNA may be directly introduced even into *E. coli* treated with calcium chloride. However, a method in which recombinant DNA is introduced into the shell of the phage in a test tube in advance (this being called "in vitro packaging") to efficiently infect the recombinant DNA with *E. coli* is generally used. Also, packaging can be performed by using a commercially available packaging kit (Gigapack II packaging extract: manufactured by Stratagene, etc.).

The packaged recombinant DNA is transfected into *E. coli*. In this instance, *E. coli* strain to be used must be selected depending on the cloning vector and plasmid vector to be used. That is, where a cloning vector containing an antibiotic resistant gene is used, *E. coli* should not have resistance to the antibiotic. On the other hand, where a cloning vector containing a gene such as α-galactosidase gene (lacZ) is used, *E. coli* which has no β-galactosidase activity must be selected.

This is necessary for screening for *E. coli* to which recombinant DNA is transfected. For example, where λgt11 cloning vector is used, it is recommended that an *E. coli* strain such as *E. coli* Y1088 be used. On the other hand, where Bluescript is used as a plasmid vector, *E. coli* JM109, etc. may be used as a host bacterium cell (indicator strain); it is just needed to suspend it together with the host bacterium cells in a soft agar medium and overlay the obtained suspension on an agar medium so as to allow plaque formation thereon. The phage plaques holding the plasmid to which a DNA fragment has been inserted do not express β-galactosidase activity so that this can be easily selected.

From the above-selected clone, the introduced vector or plasmid is prepared by a conventional method and further cleaved with an appropriate restriction enzyme to obtain the DNA1 of the present invention. The obtained cDNA fragment, as it is or after subcloning into an appropriate plasmid, is subjected to nucleotide sequencing.

One example of the nucleotide sequence of the DNA1 of the present invention thus obtained is described in SEQ ID NO: 1, and the amino acid sequence encoded thereby is described in SEQ ID NO: 2.

<4> Production Method for the Enzyme of the Present Invention

The production method for the enzyme of the present invention is a production method for the polypeptide of the enzyme or the enzyme by using the DNA1 of the present invention.

By culturing cells transfected with the above-mentioned DNA1 of the present invention, allowing the enzyme of the present invention to be generated and accumulated in the medium, and isolating the polypeptide or the enzyme containing it from the culture, the polypeptide or the enzyme containing it can be produced.

Cells transfected with the DNA1 of the present invention (transformants) can be obtained by inserting the DNA1 of the present invention into a known expression vector to construct a recombinant plasmid and performing transfection with the recombinant plasmid. The present invention provides a recombinant plasmid, i.e., a recombinant vector, containing the DNA1 of the present invention and transformants in which the DNA1 of the present invention is introduced and the DNA1 of the present invention is expressible and which can be used for the production of enzyme of the present invention and polypeptides thereof (for example, transformants transformed with the above-mentioned recombinant vector).

Examples of cell include prokaryotic cells such as *E. coli* cells and eukaryotic cells such as mammalian cells. Where prokaryotic cells such as *E. coli* cells are used, no sugar chain addition takes place to the polypeptide of the enzyme obtained by the expression of the DNA1 of the present invention, so that the polypeptide of the enzyme of the present invention can be obtained (the obtained polypeptide is particularly useful for producing antibodies). On the other hand, where eukaryotic cells such as mammalian cells are used, addition of sugar chain occurs to the above-mentioned polypeptide to produce the enzyme of the present invention.

In the method of the present invention, host-vector systems usually used in the production of proteins may be used. It is preferred to adopt combinations of cultured cells derived from mammalian cells such as COS cells (COS-1, COS-7, etc.) and 3LL-HK46 cells and expression vectors for mammalian cells, such as pcDNAI, pME18S, pCXN2, and pCEV18. However, the present invention is not particularly limited thereto and the enzyme of the present invention can also be produced by using combinations of cells of which origin is not mammalian cells with expression vectors which can be expressed in such cells. Medium and culture conditions may be appropriately selected depending on the host, i.e., cells to be used.

By using the DNA of the present invention, it is also possible to express a fused polypeptide composed of the above-mentioned polypeptide and another polypeptide.

Specific examples of the construction method for a recombinant plasmid which expresses the above-mentioned fused polypeptide include the following methods. That is, an expression plasmid vector can be constructed by inserting the DNA of the present invention so that it contains a protein such as protein A in the same reading region as that of the DNA1 of the present invention and it has a plurality of protein genes in the same reading region (for example, pGIR201protA: J. Biol. Chem. 269, 1394–1401, 1994, pcDNAI-A: J. Biol. Chem. 274, 3215–3221, 1999, etc.) and a fused polypeptide can be produced by introduction of this expression plasmid into a host cell. In addition, a DNA fragment which encodes the fused polypeptide may be cleaved out with a restriction enzyme from the expression vector and this may be ligated with another expression plasmid vector by the same operation as described above to introduce it into host cells.

Collection of the enzyme of the present invention from the culture product can be performed by a known purification method for polypeptides. Specifically, affinity chromatography using a Sepharose column having bound thereto, for example, a substrate of the above-mentioned enzyme, etc. may be mentioned. Where a fused polypeptide is expressed, purification can be performed by subjecting the culture product of host cells to affinity chromatography or the like with an affinity column having bound thereto a substance having high affinity for the polypeptide (for example, antibody, etc.) fused with the enzyme of the present invention in addition to the above-mentioned affinity column. Furthermore, by preliminarily incorporating, for example, a linker having an amino acid sequence which is recognized and cleaved by a specified proteolytic enzyme, between the polypeptides of the enzyme of the present invention and the other protein in the fused polypeptide, the enzyme of the present invention can be obtained by cleaving the fused polypeptide. As a combination of the proteolytic enzyme and the specific sequence which the proteolytic enzyme recognizes includes, for example, a combination of a signal peptidase which acts at the time of synthesis of proinsulin and a signal peptide of insulin. The above-mentioned culture product includes a medium and cultured cells.

<5> DNA2 of the Present Invention and Polypeptide Encoded Thereby

The DNA2 of the present invention is a DNA which encodes the polypeptide of human-derived HS6ST2 (hHS6ST2). Specifically, the DNA2 of the present invention is a DNA which encodes a polypeptide of the following (3) or (4):

(3) a polypeptide having an amino acid sequence as described in SEQ ID NO: 4, and (4) a polypeptide having an amino acid sequence including substitution, deletion, insertion or translocation of one or a few amino acids in the amino acid sequence of the polypeptide (3) and having an enzymatic activity of transferring sulfate from a sulfate donor to hydroxyl at position 6 of a glycosamine residue contained in a sulfate acceptor or having the same antigenicity as that of the polypeptide (3).

The DNA2 of the present invention includes, in addition to the DNA having a nucleotide sequence of SEQ ID NO: 3 or comprising a nucleotide sequence of nucleotide residues 15 to 1514 thereof, a DNA of human origin which hybridizes with the above-mentioned DNA under stringent conditions.

The DNA2 of the present invention also includes, in addition to the DNA having a nucleotide sequence of nucleotide residues 15 to 1514 of SEQ ID NO: 3 encoding the polypeptide having the amino acid sequence of SEQ ID NO: 4, variant DNAs by individual variation, single nucleotide polymorphisms (SNP), etc. of the DNA of hHS6ST2.

As the DNA2 of the present invention, DNA and RNA having nucleotide sequences complementary to the nucleotide sequence of the above-mentioned DNA are also exemplified. Further the DNAs may be either double-stranded or single-stranded and are included in the DNA2 of the present invention so far as they contain the above-mentioned nucleotide sequence or those nucleotide sequences which are complementary thereto. Also, the DNA2 of the present invention may contain the sequence of intron, which is removed before translation.

"A few" with respect to the DNA2 of the present invention is the same as described above. One skilled in the art can measure the above-mentioned enzymatic activity and antigenicity by a conventional method by using the above-mentioned enzyme of the present invention or the method described with respect to the DNA1 of the present invention and select the DNA2 of the present invention which has a polypeptide having the enzymatic activity or the antigenicity.

Preferably, the DNA2 of the present invention has a nucleotide sequence having 95% or more homology as calculated by use of a gene analysis computer programs GENETYX-MAC (manufactured by Software Development Co., Ltd.) to the nucleotide sequence of nucleotide residues 15 to 1514 of the nucleotide sequence of SEQ ID NO: 3.

The DNA2 of the present invention is a DNA which is intensively expressed in brain but substantially no intensive expression thereof is observed in testis, ovary, and kidney.

<6> Preparation Method for DNA2 of the Present Invention

The DNA2 of the present invention can be prepared by recovering an about 1,500-bp band, instead of the about 1360-bp band, from the product of the PCR method in the preparation method for DNA1 of the present invention in <4> described above.

One example of nucleotide sequence of the DNA2 of the present invention prepared in this manner is described in SEQ ID NO: 3 and the amino acid sequence encoded thereby is described in SEQ ID NO: 4.

The DNA2 of the present invention thus obtained may be introduced into a recombinant vector by using the same technique as that described in <3> above, a recombinant host cell may be prepared therewith, and human-derived HS6ST2 may be expressed in its culture product.

The thus prepared human-derived HS6ST2 has ability to form sulfated cluster (structure detected as ΔdiHS-tri(U,6,N): 2-deoxy-2-sulfamino-4-O-(4-deoxy-2-O-sulfo-α-L-threo-hex-4-enopyranosyluronic acid)-6-O-sulfo-D-glucose in disaccharide analysis) 1.2 or more times and preferably 1.5 or more times that of human derived HS6ST2v likewise prepared from the DNA1 of the present invention.

<7> Tumor Detection Method of the Present Invention

The tumor detection method of the present invention is a detection method for a tumor (tumorigenesis of tissue) characterized by relating the expression amount of the polypeptide of hHS6ST2 and/or hHS6ST2v, preferably a difference in expression amount of the polypeptide of hHS6ST2 and/or hHS6ST2v between a tumor tissue and a surrounding tissue, to the presence of a tumor in tissue cells. In particular, the measurement of a difference in total expression amount of hHS6ST2 and hHS6ST2v from healthy cells is preferred.

Measurement of the expression amount may be performed by direct measurement of the amount of polypeptide or indirect measurement by measurement of the amount of mRNA or the like. The amount of mRNA may be measured by converting mRNA into cDNA by reverse transcription.

Where the amount of polypeptide is measured, the polypeptide to be measured is usually any of polypeptides (1) to (3) described below.

(1) A polypeptide of the following {1} or {2}:

{1} a polypeptide having an amino acid sequence of SEQ ID NO: 2; and

{2} a polypeptide having an amino acid sequence including substitution, deletion, insertion or translocation of one or a few amino acids in the amino acid sequence of the polypeptide of {1} and having the same antigenicity as that of the polypeptide of {1} or having an enzymatic activity to transfer sulfate to hydroxyl at position 6 of a glycosamine residue in a glycosaminoglycan.

(2) A polypeptide having an amino acid sequence including substitution, deletion, insertion or translocation of one or a few amino acids in the amino acid sequence of SEQ ID NO: 2, in which the polypeptide has an enzymatic activity to transfer sulfate to hydroxyl at position 6 of a glycosamine residue in a glycosaminoglycan and also has a ratio of relative activities to substrates satisfying N-Sulfated (NS) heparosan/Completely Desulfated N-Sulfated (CDSNS) heparin ≧1.90.

(3) A polypeptide of the following {3} or {4}:

{3} a polypeptide having an amino acid sequence of SEQ ID NO: 4; and

{4} a polypeptide having an amino acid sequence including substitution, deletion, insertion or translocation of one or a few amino acids in the amino acid sequence of the polypeptide of {3} and having an enzymatic activity to transfer sulfate to hydroxyl at position 6 of a glycosamine residue in a glycosaminoglycan or having the same antigenicity as that of the polypeptide of {3}.

In the case where the amount of mRNA is measured, the measured mRNA is usually one generated by transcription of the DNA of the following {1} or {2}.

(1) A DNA selected from any one of the following (a) to (d):

(a) a DNA having a nucleotide sequence of SEQ ID NO: 1;

(b) a DNA having a nucleotide sequence of nucleotide residues 2 to 1381 of the nucleotide sequence of SEQ ID NO: 1;

(c) a DNA having a nucleotide sequence which is complementary to the nucleotide sequence of the DNA of (a) or (b);

(d) a DNA which hybridizes with the DNA of (a), (b) or (c) above under stringent conditions, the DNA encoding a polypeptide which has an enzymatic activity to transfer sulfate to hydroxyl at position 6 of a glycosamine residue in a glycosaminoglycan.

(2) A DNA selected from any one of the following (e) to (h):

(e) a DNA having a nucleotide sequence of SEQ ID NO: 3;

(f) a DNA having a nucleotide sequence of nucleotide residues 15 to 1514 of the nucleotide sequence of SEQ ID NO: 3;

(g) a DNA having a nucleotide sequence which is complementary to the nucleotide sequence of the DNA of (e) or (f); and (h) a human-derived DNA which hybridizes with the DNA of (e), (f) or (g) above under stringent conditions.

According to one embodiment of the present invention, a tissue having a high possibility of containing a tumor and a healthy tissue surrounding it are collected by, for example, biopsy, etc., from which cDNAs are prepared in accordance with a conventional method. The expression amounts of hHS6ST2 and hHS6ST2v are compared, for example, by a hybridization method using a DNA having a nucleotide sequence of residues 15 to 1514 of the nucleotide sequence of SEQ ID NO: 3 as a probe. The results of the comparison and presence of tumor are related to each other and the presence of tumor is detected.

For example, in brain, small intestine, kidney and soft tissue, where a sample tissue has decreased expression amounts of polypeptides of hHS6ST2 and hHS6ST2v as compared with those of healthy tissue, it can be judged that a tumor is present in that tissue. On the other hand, in lung glandular tissue, large intestine, and adrenal gland, where a sample tissue has increased expression amounts of polypeptides of hHS6ST2 and hHS6ST2v as compared with those of healthy tissue, it can be judged that a tumor is present in that tissue.

EXAMPLE

Hereinafter, the present invention will be described in more detail by examples.

Example 1

Preparation of DNA of the Present Invention (1) Preparation of Primer and Amplification of DNA By using the amino acid sequence of mouse HS6ST2 (mHS6ST2) (J. Biol. Chem., 275, 2859–2868 (2000)), dbEST of GenBank was searched to find a human counterpart DNA having a homology to encoded amino acid sequence (GenBank accession No. AL049679). A primer (Pr1: SEQ ID NO: 5) having a nucleotide sequence of nucleotide residues (−14) to (6) of the nucleotide sequence encoding mHS6ST (J. Biol. Chem., 275, 2859–2868 (2000)) as counted taking the translation initiation site as 1 and a primer (Pr2: SEQ ID NO: 6) having a nucleotide sequence complementary to a nucleotide sequence of nucleotide residues 1481–1500 of the nucleotide sequence of GenBank accession No. AL049679 were synthesized. With these, DNA was amplified by a PCR method with human brain cDNA manufactured by Stratagene as a template and Taq PCR Core Kit (manufactured by Qiagen, K.K.). The PCR method was performed under conditions of denaturation reaction at 94° C. for 30 seconds, annealing at 55° C. for 30 seconds and elongation reaction at 72° C. for 2 minutes. This was performed in 35 cycles. Thereafter, elongation reaction was performed for further 15 minutes. Upon analysis of the amplification product obtained by this operation by Agarose gel electrophoresis, two amplified DNA bands of about 1,360 bp and of about 1,500 bp were detected.

(2) Subcloning of PCR Product and Determination of Nucleotide Sequence

From the gel described above, DNA present in each band was recovered by using Jetsorb (manufactured by Genomed, Inc.). The nucleotide sequence of the amplified DNA was directly determined from the recovered DNA. Nucleotide sequences were determined by using dGTP/deazaGTP kit containing Sequenase version 2.0 (U.S. Biochemical Corporation). The nucleotide sequences were edited and analyzed by means of a computer program GENETYX-MAC. It was revealed that the PCR products have open reading frames, respectively. The determined nucleotide sequences are shown in SEQ ID NO: 1 and SEQ ID NO: 3, respectively, and amino acid sequences encoded by the open reading frames are shown in SEQ ID NO: 2 and SEQ ID NO: 4, respectively.

The larger PCR product was revealed to be a cDNA of hHS6ST2 having 98% homology to mHS6ST (DNA2 of the present invention) and the smaller PCR product had a nucleotide sequence corresponding to cDNA of hHS6ST2 but lacking 117 base pairs present in the intermediate portion thereof, which was revealed to be a variant (hHS6ST2v) of hHS6ST2 (DNA1 of the present invention). The 117 base pairs which are present in hHS6ST2 and in which hSH6ST2v is deficient were found to be a nucleotide sequence corresponding to the second and third exons of mHS6ST2 by comparison with the results of exon/intron analysis of a genomic DNA of mHS6ST2.

Results of comparisons of the polypeptides of hHS6ST2, hHS6ST2v and mHS6ST2 are shown in Table 1. Homology was calculated based on mHS6ST2 as a standard by using a gene analysis computer program GENETYX-MAC (manufactured by Software Development Co., Ltd.).

TABLE 1

| Comparison of polypeptide | | | |
|---|---|---|---|
| | hHS6ST2 | hHS6ST2v | mHS6ST2 |
| Number of amino acids | 499 | 459 | 506 |
| Molecular weight | 57696 | 53459 | 58092 |
| N-Linked glycosylation site | 9 | 8 | 9 |
| Homology to mHS6ST-2 | 92% | 86% | 100% |
| PAPS-binding site | Present | Present | Present |

Example 2

Preparation of the Enzyme of the Present Invention (1) Preparation of Plasmid for Expression of the Enzyme of the Present Invention To express the cDNA of hHS6ST2, a cDNA fragment was inserted into an expression vector to construct a recombinant plasmid. The isolated cDNA of hHS6ST2v was introduced into HindIII/EcoRI site of pFLAG-CMV-2 (manufactured by Eastman Kodak Company), which was an expression vector for a mammalian, to construct a recombinant plasmid, pFLAG-CMV-2hHS6ST2v. This plasmid was constructed so as to express a fused polypeptide of FLAG which is a sequence as a tag having no activity of enzyme or the like and hHS6ST2v.

(2) Transient Expression of cDNA of hHS6ST2v in COS-7 Cells

As a host for expressing cDNA of hHS6ST2v, COS-7 cells were used. COS-7 cells were suspended in 3 ml of Dulbecco's modified Eagle medium (manufactured by Life Technologies, Inc.) containing 50 units/ml of penicillin, 50 μg/ml of streptomycin, and 10% (v/v) fetal calf serum and transfected with the expression vector produced as described above by DEAE-dextran method (Aruffo, A., Current Protocols in Molecular Biology, 1992, Supplement 14, Unit 16.13.1–16.13.7, Green Publishing Associates/Wiley-Interscience, New York), and thereafter, cultured under the condition of 37° C.

The cells transfected with pFLAG-CMV-2hHS6ST2v were cultured for 67 hours and from these cells a cell extract was prepared by the method described in Habuchi, H., Habuchi, O., and Kimata, K. (1995) J. Biol. Chem. 270, 4172–4179. From the cell extract, hHS6ST2v was purified and isolated by affinity chromatography with an anti-FLAG antibody and its substrate specificity was studied (Table 2). The measurement of activity was performed according to the method described in Habuchi, H., Habuchi, O., and Kimata, K. (1995) J. Biol. Chem. 270, 4172–4179 and Kobayashi, M., Habuchi, H., Habuchi, O., Saito, M., and Kimata, K. (1996) J. Biol. Chem. 271, 7645–7653, by using various sulfate acceptors as substrates and measuring enzymatic activity on each of them. The results are shown in relative values taking the activity on CDSNS heparin as 100. As controls for comparison, mHS6ST2 and hHS6ST2 isolated from COS-7 cells transfected with pFLAG-CMV-2 in which mHS6ST2 was introduced in the same manner as hHS6ST2v described above (pFLAG-CMV-2 mHS6ST2) and COS-7 cells transfected with pFLAG-CMV-2 in which hHS6ST2 was introduced in the same manner (pFLAG-CMV-2hHS6ST2) by the same purification method as that described above were used.

TABLE 2

| Substrate specificity | | | |
|---|---|---|---|
| | HS6ST activity | | |
| Substrate | hHS6ST2v | hHS6ST2 | mHS6ST2 |
| CDSNS heparin | 100 | 100 | 100 |
| NS heparosan | 278 | 202 | 185 |
| Heparin | 2.1 | 2.4 | 8.6 |
| CDSNAc heparin | 7.5 | 8.2 | 4.7 |
| Heparan sulfate (porcine artery) | 91 | 84 | 65 |
| Heparan sulfate (Mouse EHS tumor) | 155 | 106 | 97 |

*Not active on chondroitin sulfate A and chondroitin sulfate C.

It becomes evident that hHS6ST2v has higher sulfotransferase activities on NS heparosan, heparin, and CDSNAc heparin than those of mHS6ST2.

Heparan sulfate from porcine artery was weighed so as to contain 25 nmol of uronic acid. 50 pmol of radioactivity-labeled active sulfate ({$^{35}$S}PAPS) and 0.35 U (amount necessary for sulfating CDSNS heparin in a rate of 0.35 pmol/min) of hHS6ST2 (prepared in the same manner as the hHS6ST2v described above with a cDNA of hHS6ST2), hHS6ST2v, or HS6ST1 (J. Biol. Chem., Vol. 270 (1995), pp. 4172–4179) as a control for comparison was added thereto and reaction was carried out at 20° C. for 1 hour. After boiling the reaction mixture to inactivate the enzyme, chondroitin sulfate A (CSA: manufactured by Seikagaku Corporation) was added and unreacted {$^{35}$S}PAPS was removed by an ethanol precipitation method. Here, heparan sulfate modified with HS6ST2 was named HS2, heparan sulfate modified with HS6ST2v was named HS2v, and heparan sulfate modified with HS6ST1 was named HS1.

HS2, HS2v, and HS1 were fractionated by a combination of digestion with heparin-degrading enzymes and high performance liquid chromatography. That is, 1.0 μg of the test substance was dissolved in 25 μg of 20 mM sodium acetate (pH 7.0) containing 2 mM of calcium acetate. Each 1.5 mU of heparitinase and of heparitinase I as well as 0.15 mU of heparitinase II (all manufactured by Seikagaku Corporation) were added thereto and reaction was carried out at 37° C. for 1 hour.

Figure 2:
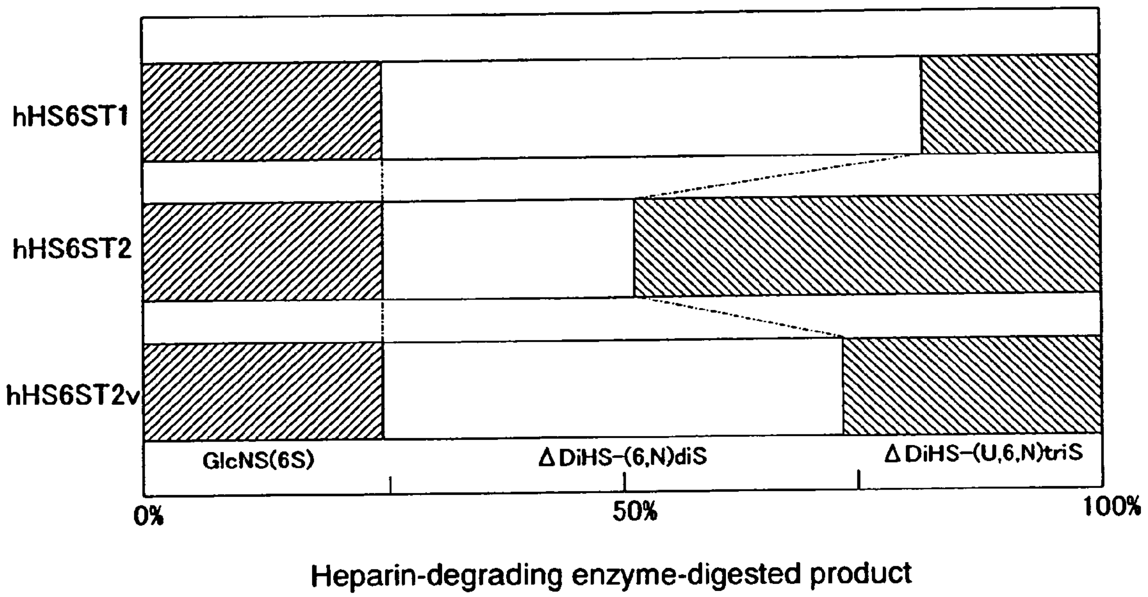
FIG. 2 shows results of comparisons of the ability to form sulfated clusters among hHS6ST2, hHS6ST2v, and hHS6ST1 based on the results shown in FIG. 1.

The reaction mixtures were analyzed by using HPLC (manufactured by Waters Corporation) under the following conditions. That is, a silica-based amino column (manufactured by YMC Corporation; YMC-Pack Polyamine-II column ϕ 4.0×250 mm) was used, and elution was performed by a concentration gradient method with sodium dihydrogen phosphate (250 mM→540 mM) at a flow rate of 1.2 ml/minute according to the method of Habuchi, et al. (Habuchi, et al. (1992) Biochem. J., 285, pp.805–813), and absorbance of the eluation was measured at 232 nm. Fractions from 16 minutes to 43 minutes were recovered and then the radioactivity in each fraction was measured by a scintillation counter (FIG. 1). In FIG. 1, ΔDiHS-6S indicates 2-acetamido-2-deoxy-4-O-(4-deoxy-α-L-threo-hex-4-enopyranosyluronic acid)-6-O-sulfo-D-glucose; ΔDiHS-NS indicates 2-deoxy-2-sulfamino-4-O-(4-deoxy-α-L-threo-hex-4-enopyranosyluronic acid)-D-glucose; ΔDiHS-di(6,N)S indicates 2-deoxy-2-sulfamino-4-O-(4-deoxy-α-L-threo-hex-4-enopyranosyluronic acid)-6-O-sulfo-D-glucose; ΔDiHS-di(N,U)S indicates 2-deoxy-2-sulfamino-4-O-(4-deoxy-2-O-sulfo-α-L-threo-hex-4-enopyranosyluronic acid)-D-glucose; and ΔDiHS-tri(U,6,N)S indicates 2-deoxy-2-sulfamino-4-O-(4-deoxy-2-O-sulfo-α-L-threo-hex-4-enopyranosyluronic acid)-6-O-sulfo- D-glucose. From the count number of the scintillation counter, hHS6ST2, hHS6ST2v, and hHS6ST1 were compared by the peak of unsaturated disaccharide (Δdi-(N,6,U) triS) having the structure in which 2-O-sulfated uronic acid and 6,N-sulfated glucosamine are bound (the peak indicating ability to form sulfated cluster), standardized by the peak of N-acetylglucosamine residue having a sulfate group at position 6 (peak at 19 minutes) (FIG. 2). As a result, it was revealed that hHS6ST2v had an ability to form sulfated cluster to an extent moderate between hHS2ST2 and hHS6ST1.

Example 3

Observation of HS6ST2 Expression in Tumors

Figure 3:
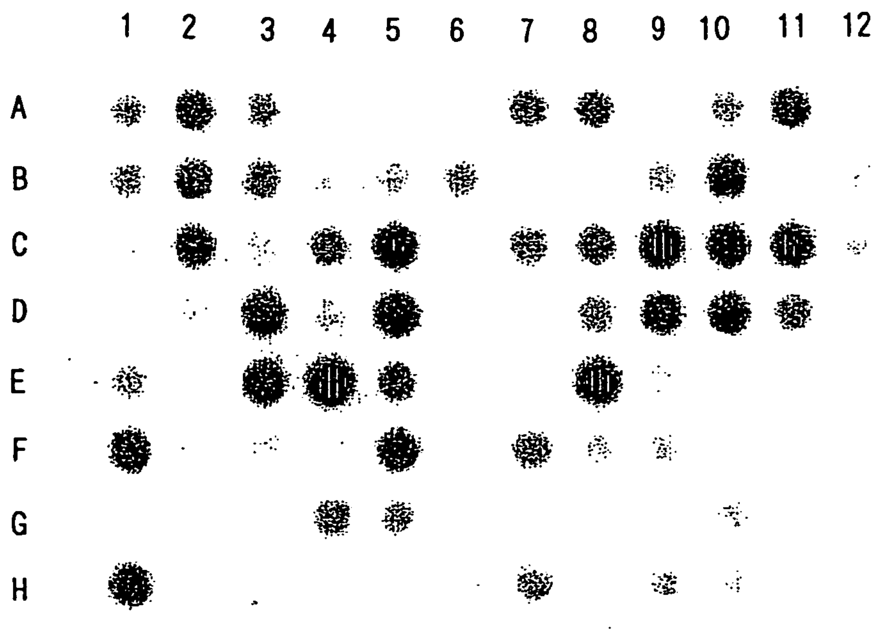
FIG. 3 is a photograph showing results of analysis of hHS6ST2 expression by a hybridization method using a total RNA dot blotting membrane for human tumor tissues.

By using a total RNA dot blotting membrane for human tumor tissues (manufactured by Bio Chain, Inc.), expression of HS6ST2 was analyzed by a hybridization method (expression hybridization method) with a portion of the nucleotide sequence of the coding region of hHS6ST2 (nucleotide residues 15–1514 of the nucleotide sequence of SEQ ID NO: 3) (FIG. 3). The arrangement of tissues on the blotting membrane is as shown in Table 3. Under the conditions used, total expression amounts of hHS6ST2 and hHS6ST2v are detected.

As a result, it was revealed that in tumor sites in brain, small intestine, kidney and soft tissue, the expression amounts of hHS6ST2 and hHS6ST2v were clearly decreased as compared with those in surrounding healthy tissues while these were increased in tumor sites in lung glandular tissue, large intestine and adrenal gland. These results suggest a possibility that the presence of a tumor in each tissue when the expression amounts of hHS6ST2 and hHS6ST2v in tissue samples are decreased as compared with those of healthy tissues in the case of brain, small intestine, kidney and soft tissue and when the expression amounts of hHS6ST2 and hHS6ST2v are increased in tissue samples as compared with those of healthy tissues in the case of lung glandular tissue, large intestine and adrenal gland.

Figure 4:
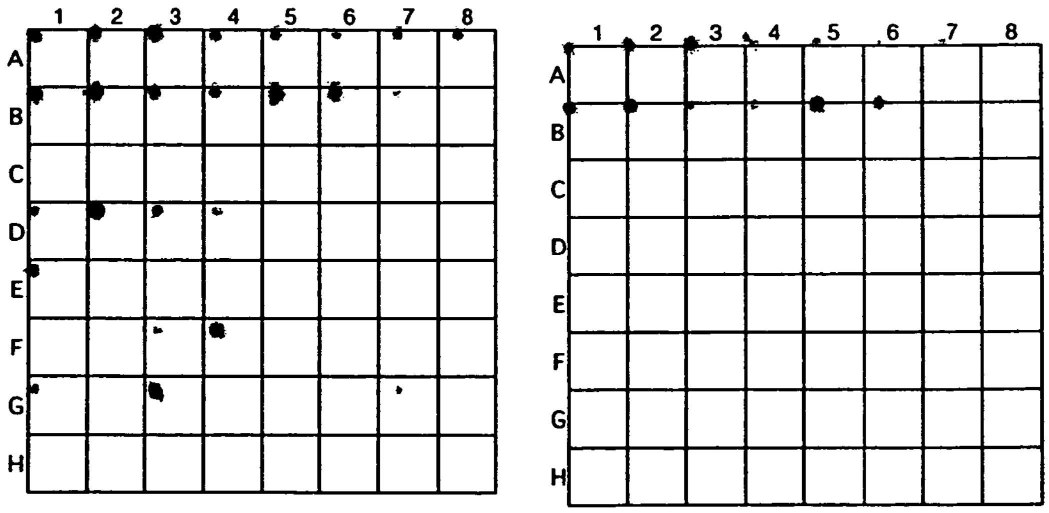
FIG. 4 is a photograph showing results of analyses of expression of hHS6ST2 and hHS6ST2v, or hHS6ST2 by a hybridization method using a total RNA dot blotting membrane for healthy human tissues. Left: hHS6ST2 and hHS6ST2v, right: hHS6ST2.

In the same manner as described above, by using a total RNA dot blotting membrane for human healthy tissues (manufactured by Bio Chain, Inc.), expressions of HS6ST2 and HS6ST2v or expression of HS6ST2 was analyzed by a hybridization method (expression hybridization method) with a portion of the nucleotide sequence of the coding region of hHS6ST2 (nucleotide residues 15–1514 of the nucleotide sequence of SEQ ID NO: 3) or of hHS6ST2 (nucleotide residues 525–644 of the nucleotide sequence of SEQ ID NO: 3), respectively, (FIG. 4). The arrangement of tissues on the blotting membrane is as shown in Table 4.

TABLE 3

Arrangement of tissues on blot membrane

| | 1&2 | 3&4 | 5&6 | 7&8 | 9&10 | 11&12 |
|---|---|---|---|---|---|---|
| A | Brain<br>1. Astrocytoma<br>2. Normal | Pharynx/Throat<br>3. Squamous cell carcinoma<br>4. Normal | Duodenum<br>5. Tumor<br>6. Normal | Gallbladder<br>7. Tumor<br>8. Normal | Testis<br>9. Tumor<br>10. Normal | Thyroid gland<br>11. Follicular adenocarcinoma<br>12. Normal |
| B | Brain<br>1. Neurilemmoma<br>2. Normal | Esophagus<br>3. Poorly differentiated squamous cell carcinoma<br>4. Normal | Small Intestine<br>5. Tumor<br>6. Normal | Pancreas<br>7. Tumor<br>8. Normal | Ovary<br>9. Adenocarcinoma<br>10. Normal | Thyroid gland<br>11. Follicular adenoma<br>12. Normal |
| C | Brain<br>1. Meningioma<br>2. Normal | Esophagus<br>3. Moderately differentiated squamous cell carcinoma<br>4. Normal | Colon<br>5. Poorly differentiated adenocarcinoma<br>6. Normal | Parotid gland<br>7. Tumor<br>8. Normal | Ovary<br>9. Thecoma<br>10. Normal | Thyroid gland<br>11. Papillary adenocarcinoma<br>12. Normal |
| D | Lung<br>1. Poorly differentiated squamous cell carcinoma<br>2. Normal | Esophagus<br>3. Adenocarcinoma<br>4. Normal | Colon<br>5. Well differentiated adenocarcinoma<br>6. Normal | Kidney<br>7. Granular cell carcinoma<br>8. Normal | Ovary<br>9. Teratoma<br>10. Normal | Adrenal gland<br>11. Tumor<br>12. Normal |
| E | Lung<br>1. Moderately differentiated squamous cell carcinoma<br>2. Normal | Stomach<br>3. Squamous cell carcinoma<br>4. Normal | Rectum<br>5. Poorly differentiated adenocarcinoma<br>6. Normal | Kidney<br>7. Clear cell carcinoma<br>8. Normal | Uterus<br>9. Leiomyoma<br>10. Normal | Thymus<br>11. Tumor<br>12. Normal |
| F | Lung<br>1. Poorly differentiated adenocarcinoma<br>2. Normal | Stomach<br>3. Poorly differentiated adenocarcinoma<br>4. Normal | Rectum<br>5. Moderately differentiated adenocarcinoma<br>6. Normal | Bladder<br>7. Transitional cell carcinoma grade II<br>8. Normal | Uterus<br>9. Adenocarcinoma<br>10. Normal | Lymphoma<br>11. Lymphoma<br>12. Normal lymph node |
| G | Lung<br>1. Moderately differentiated adenocarcinoma<br>2. Normal | Stomach<br>3. Moderately differentiated adenocarcinoma<br>4. Normal | Liver<br>5. Poorly differentiated hepatocellular carcinoma<br>6. Normal | Bladder<br>7. Transitional cell carcinoma grade III<br>8. Normal | Breast<br>9. invasive ductal carcinoma<br>10. Normal | Non-Hodgkin's lymphoma<br>11. Lymphoma<br>12. Normal lymph node |
| H | Lung<br>1. Alveolar carcinoma<br>2. Normal | Stomach<br>3. Well differentiated adenocarcinoma<br>4. Normal | Liver<br>5. Moderately differentiated hepatocellular carcinoma<br>6. Normal | Prostate<br>7. Tumor<br>8. Normal | Breast<br>9. Fibroadenoma<br>10. Normal | Soft tissue<br>11. Malignant fibrous histocytoma<br>12. Normal |

TABLE 4

| | 1 | 2 | 3 | 4 | 5 | 6 | 7 | 8 |
|---|---|---|---|---|---|---|---|---|
| A | Entire brain | Amygdala | Caudate nucleus | Cerebellum | Cerebral cortex | Frontal lobe | Hippocampus | Medulla oblongata |
| B | Occipital lobe | Putamen | Substantia nigra | Temporal lobe | Thalamus | Subthalamic nucleus | Spinal cord | |
| C | Heart | Aorta | Skeletal muscle | Colon | Bladder | Uterus | Prostate | Stomach |
| D | Testis | Ovary | Pancreas | Pituitary gland | Adrenal gland | Thyroid gland | Salivary gland | Mammary gland |
| E | Kidney | Liver | Small intestine | Spleen | Thymus | Peripheral leukocyte | Lymph node | Bone marrow |
| F | Appendix | Lung | Trachea | Placenta | | | | |
| G | Fetal brain | Fetal heart | Fetal kidney | Fetal liver | Fetal spleen | Fetal thymus | Fetal lung | |
| H | Yeast total RNA (100 μg) | Yeast tRNA (100 μg) | *E. coli* rRNA (100 μg) | *E. coil* DNA (100 μg) | Poly-r(A) (100 μg) | Human Col DNA (100 μg) | Human DNA (100 μg) | Human DNA (500 μg) |

As a result, it was revealed that hHS6ST2 and hHS6ST2v were expressed intensively in central nerves (brain and its appendages), testis, ovary, kidney, and placenta (FIG. 4, left). Also, it was revealed that hHS6ST2 was intensively expressed particularly in a broad region of brain (FIG. 4, right).

INDUSTRIAL APPLICABILITY

According to the present invention, novel isoforms of human sulfotransferase and DNAs encoding them are provided. Furthermore, tumorigenesis of tissues can be detected based on the expression amounts of the isoforms.

What is claimed is:

1. An isolated polypeptide having the amino acid sequence of SEQ ID NO: 4.

* * * * *

UNITED STATES PATENT AND TRADEMARK OFFICE

CERTIFICATE OF CORRECTION

PATENT NO. : 7,150,981 B2
APPLICATION NO. : 10/312892
DATED : December 19, 2006
INVENTOR(S) : Habuchi et al.

It is certified that error appears in the above-identified patent and that said Letters Patent is hereby corrected as shown below:

Page 1, Line 1, Title, "SULFATE TRANSFERASE AND DNA ENCODING THIS ENZYME" should be changed to --SULFOTRANSFERASE AND DNA ENCODING THE ENZYME--

Column 1, Lines 1-2, "SULFATE TRANSFERASE AND DNA ENCODING THIS ENZYME" should be changed to --SULFOTRANSFERASE AND DNA ENCODING THE ENZYME--

Column 5, Line 11, "CDSNAC heparin" should be changed to --CDSNAc heparin--

Column 8, Line 9, "nuleotide sequence" should be changed to --nucleotide sequence--

Column 9, Line 36, "such as α-galactosidase" should be changed to --such as β-galactosidase--

Column 16, Line 39, "in 25 μg of" should be changed to --in 25 μl of--

Columns 17-18, Table 3 (Column 9&10), "Breast
9. invasive
ductal carcinoma" should be changed to --Breast
9. Invasive
ductal carcinoma--

UNITED STATES PATENT AND TRADEMARK OFFICE

CERTIFICATE OF CORRECTION

PATENT NO. : 7,150,981 B2 
APPLICATION NO. : 10/312892
DATED : December 19, 2006
INVENTOR(S) : Habuchi et al.

It is certified that error appears in the above-identified patent and that said Letters Patent is hereby corrected as shown below:

Columns 19-20, Table 4 (Column 4), "Placenta
Fetal
liver
*E. coil*
DNA
(100 μg)" should be changed to --Placenta
Fetal
liver
*E. coli*
DNA
(100 μg)--

Signed and Sealed this

Twenty-second Day of May, 2007

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 1381
<212> TYPE: DNA
<213> ORGANISM: Homo sapiens
<220> FEATURE:
<221> NAME/KEY: CDS
<222> LOCATION: (2)..(1378)

<400> SEQUENCE: 1

c atg gat gag aaa tcc aac aag ctg ctg cta gct ttg gtg atg ctc ttc      49
  Met Asp Glu Lys Ser Asn Lys Leu Leu Leu Ala Leu Val Met Leu Phe
    1               5                  10                  15

cta ttt gcc gtg atc gtc ctc caa tac gtg tgc ccc ggc aca gaa tgc        97
Leu Phe Ala Val Ile Val Leu Gln Tyr Val Cys Pro Gly Thr Glu Cys
                20                  25                  30

cag ctc ctc cgc ctg cag gcg ttc agc tcc ccg gtg ccg gac ccg tac       145
Gln Leu Leu Arg Leu Gln Ala Phe Ser Ser Pro Val Pro Asp Pro Tyr
            35                  40                  45

cgc tcg gag gat gag agc tcc gcc agg ttc gtg ccc cgc tac aat ttc       193
Arg Ser Glu Asp Glu Ser Ser Ala Arg Phe Val Pro Arg Tyr Asn Phe
        50                  55                  60

acc cgc ggc gac ctc ctg cgc aag gta gac ttc gac atc aag ggc gat       241
Thr Arg Gly Asp Leu Leu Arg Lys Val Asp Phe Asp Ile Lys Gly Asp
 65                  70                  75                  80

gac ctg atc gtg ttc ctg cac atc cag aag acc ggg ggc acc act ttc       289
Asp Leu Ile Val Phe Leu His Ile Gln Lys Thr Gly Gly Thr Thr Phe
                 85                  90                  95

ggc cgc cac ttg gtg cgt aac atc cag ctg gag cag ccg tgc gag tgc       337
Gly Arg His Leu Val Arg Asn Ile Gln Leu Glu Gln Pro Cys Glu Cys
            100                 105                 110

cgc gtg ggt cag aag aaa tgc act tgc cac cgg ccg ggt aag cgg gaa       385
Arg Val Gly Gln Lys Lys Cys Thr Cys His Arg Pro Gly Lys Arg Glu
        115                 120                 125
```

-continued

```
acc tgg ctc ttc tcc agg ttc tcc acg ggc tgg agc tgc ggg ttg cac       433
Thr Trp Leu Phe Ser Arg Phe Ser Thr Gly Trp Ser Cys Gly Leu His
    130                 135                 140

gcc gac tgg acc gag ctc acc agc tgt gtg ccc tcc gtg gtg gac ggc       481
Ala Asp Trp Thr Glu Leu Thr Ser Cys Val Pro Ser Val Val Asp Gly
145                 150                 155                 160

aag cgc gac gcc agg ctg aga ccg tcc agg aac ttc cac tac atc acc       529
Lys Arg Asp Ala Arg Leu Arg Pro Ser Arg Asn Phe His Tyr Ile Thr
                165                 170                 175

atc ctc cga gac cca gtg tcc cgg tac ttg agt gag tgg agg cat gtc       577
Ile Leu Arg Asp Pro Val Ser Arg Tyr Leu Ser Glu Trp Arg His Val
            180                 185                 190

cag aga ggg gca aca tgg aaa gca tcc ctg cat gtc tgc gat gga agg       625
Gln Arg Gly Ala Thr Trp Lys Ala Ser Leu His Val Cys Asp Gly Arg
        195                 200                 205

cct cca acc tcc gaa gag ctg ccc agc tgc tac act ggc gat gac tgg       673
Pro Pro Thr Ser Glu Glu Leu Pro Ser Cys Tyr Thr Gly Asp Asp Trp
    210                 215                 220

tct ggc tgc ccc ctc aaa gag ttt atg gac tgt ccc tac aat cta gcc       721
Ser Gly Cys Pro Leu Lys Glu Phe Met Asp Cys Pro Tyr Asn Leu Ala
225                 230                 235                 240

aac aac cgc cag gtg cgc atg ctc tcc gac ctg acc ctg gta ggc tgc       769
Asn Asn Arg Gln Val Arg Met Leu Ser Asp Leu Thr Leu Val Gly Cys
                245                 250                 255

tac aac ctc tct gtc atg cct gaa aag caa aga aac aag gtc ctt ctg       817
Tyr Asn Leu Ser Val Met Pro Glu Lys Gln Arg Asn Lys Val Leu Leu
            260                 265                 270

gaa agt gcc aag tca aat ctg aag cac atg gcg ttc ttc ggc ctc act       865
Glu Ser Ala Lys Ser Asn Leu Lys His Met Ala Phe Phe Gly Leu Thr
        275                 280                 285

gag ttt cag cgg aag acc caa tat ctg ttt gag aaa acc ttc aac atg       913
Glu Phe Gln Arg Lys Thr Gln Tyr Leu Phe Glu Lys Thr Phe Asn Met
    290                 295                 300

aac ttt att tcg cca ttt acc cag tat aat acc act agg gcc tct agt       961
Asn Phe Ile Ser Pro Phe Thr Gln Tyr Asn Thr Thr Arg Ala Ser Ser
305                 310                 315                 320

gta gag atc aat gag gaa att caa aag cgt att gag gga ctg aat ttt      1009
Val Glu Ile Asn Glu Glu Ile Gln Lys Arg Ile Glu Gly Leu Asn Phe
                325                 330                 335

ctg gat atg gag ttg tac agc tat gcc aaa gac ctt ttt ttg cag agg      1057
Leu Asp Met Glu Leu Tyr Ser Tyr Ala Lys Asp Leu Phe Leu Gln Arg
            340                 345                 350

tat cag ttt atg agg cag aaa gag cat cag gag gcc agg cga aag cgt      1105
Tyr Gln Phe Met Arg Gln Lys Glu His Gln Glu Ala Arg Arg Lys Arg
        355                 360                 365

cag gaa caa cgc aaa ttt ctg aag gga agg ctc ctt cag acc cat ttc      1153
Gln Glu Gln Arg Lys Phe Leu Lys Gly Arg Leu Leu Gln Thr His Phe
    370                 375                 380

cag agc cag ggt cag ggc cag agc cag aat ccg aat cag aat cag agt      1201
Gln Ser Gln Gly Gln Gly Gln Ser Gln Asn Pro Asn Gln Asn Gln Ser
385                 390                 395                 400

cag aac cca aat ccg aat gcc aat cag aac ctg act cag aat ctg atg      1249
Gln Asn Pro Asn Pro Asn Ala Asn Gln Asn Leu Thr Gln Asn Leu Met
                405                 410                 415

cag aat ctg act cag agt ttg agc cag aag gag aac cgg gaa agc ccg      1297
Gln Asn Leu Thr Gln Ser Leu Ser Gln Lys Glu Asn Arg Glu Ser Pro
            420                 425                 430

aag cag aac tca ggc aag gag cag aat gat aac acc agc aat ggc acc      1345
Lys Gln Asn Ser Gly Lys Glu Gln Asn Asp Asn Thr Ser Asn Gly Thr
```

-continued

```
        435                 440                 445

aac gac tac ata ggc agt gta gag aaa tgg cgt taa                     1381
Asn Asp Tyr Ile Gly Ser Val Glu Lys Trp Arg
    450                 455


<210> SEQ ID NO 2
<211> LENGTH: 459
<212> TYPE: PRT
<213> ORGANISM: Homo sapiens

<400> SEQUENCE: 2

Met Asp Glu Lys Ser Asn Lys Leu Leu Leu Ala Leu Val Met Leu Phe
  1               5                  10                  15

Leu Phe Ala Val Ile Val Leu Gln Tyr Val Cys Pro Gly Thr Glu Cys
             20                  25                  30

Gln Leu Leu Arg Leu Gln Ala Phe Ser Ser Pro Val Pro Asp Pro Tyr
         35                  40                  45

Arg Ser Glu Asp Glu Ser Ser Ala Arg Phe Val Pro Arg Tyr Asn Phe
     50                  55                  60

Thr Arg Gly Asp Leu Leu Arg Lys Val Asp Phe Asp Ile Lys Gly Asp
 65                  70                  75                  80

Asp Leu Ile Val Phe Leu His Ile Gln Lys Thr Gly Gly Thr Thr Phe
                 85                  90                  95

Gly Arg His Leu Val Arg Asn Ile Gln Leu Glu Gln Pro Cys Glu Cys
            100                 105                 110

Arg Val Gly Gln Lys Lys Cys Thr Cys His Arg Pro Gly Lys Arg Glu
        115                 120                 125

Thr Trp Leu Phe Ser Arg Phe Ser Thr Gly Trp Ser Cys Gly Leu His
    130                 135                 140

Ala Asp Trp Thr Glu Leu Thr Ser Cys Val Pro Ser Val Val Asp Gly
145                 150                 155                 160

Lys Arg Asp Ala Arg Leu Arg Pro Ser Arg Asn Phe His Tyr Ile Thr
                165                 170                 175

Ile Leu Arg Asp Pro Val Ser Arg Tyr Leu Ser Glu Trp Arg His Val
            180                 185                 190

Gln Arg Gly Ala Thr Trp Lys Ala Ser Leu His Val Cys Asp Gly Arg
        195                 200                 205

Pro Pro Thr Ser Glu Glu Leu Pro Ser Cys Tyr Thr Gly Asp Asp Trp
    210                 215                 220

Ser Gly Cys Pro Leu Lys Glu Phe Met Asp Cys Pro Tyr Asn Leu Ala
225                 230                 235                 240

Asn Asn Arg Gln Val Arg Met Leu Ser Asp Leu Thr Leu Val Gly Cys
                245                 250                 255

Tyr Asn Leu Ser Val Met Pro Glu Lys Gln Arg Asn Lys Val Leu Leu
            260                 265                 270

Glu Ser Ala Lys Ser Asn Leu Lys His Met Ala Phe Phe Gly Leu Thr
        275                 280                 285

Glu Phe Gln Arg Lys Thr Gln Tyr Leu Phe Glu Lys Thr Phe Asn Met
    290                 295                 300

Asn Phe Ile Ser Pro Phe Thr Gln Tyr Asn Thr Thr Arg Ala Ser Ser
305                 310                 315                 320

Val Glu Ile Asn Glu Glu Ile Gln Lys Arg Ile Glu Gly Leu Asn Phe
                325                 330                 335

Leu Asp Met Glu Leu Tyr Ser Tyr Ala Lys Asp Leu Phe Leu Gln Arg
            340                 345                 350
```

-continued

Tyr Gln Phe Met Arg Gln Lys Glu His Gln Glu Ala Arg Arg Lys Arg
355 360 365

Gln Glu Gln Arg Lys Phe Leu Lys Gly Arg Leu Leu Gln Thr His Phe
370 375 380

Gln Ser Gln Gly Gln Gly Gln Ser Gln Asn Pro Asn Gln Asn Gln Ser
385 390 395 400

Gln Asn Pro Asn Pro Asn Ala Asn Gln Asn Leu Thr Gln Asn Leu Met
405 410 415

Gln Asn Leu Thr Gln Ser Leu Ser Gln Lys Glu Asn Arg Glu Ser Pro
420 425 430

Lys Gln Asn Ser Gly Lys Glu Gln Asn Asp Asn Thr Ser Asn Gly Thr
435 440 445

Asn Asp Tyr Ile Gly Ser Val Glu Lys Trp Arg
450 455

<210> SEQ ID NO 3
<211> LENGTH: 1514
<212> TYPE: DNA
<213> ORGANISM: Homo sapiens
<220> FEATURE:
<221> NAME/KEY: CDS
<222> LOCATION: (15)..(1511)

<400> SEQUENCE: 3
ccagcgtcgg gaac atg gat gag aaa tcc aac aag ctg ctg cta gct ttg 50
Met Asp Glu Lys Ser Asn Lys Leu Leu Leu Ala Leu
1 5 10 gtg atg ctc ttc cta ttt gcc gtg atc gtc ctc caa tac gtg tgc ccc 98
Val Met Leu Phe Leu Phe Ala Val Ile Val Leu Gln Tyr Val Cys Pro
15 20 25 ggc aca gaa tgc cag ctc ctc cgc ctg cag gcg ttc agc tcc ccg gtg 146
Gly Thr Glu Cys Gln Leu Leu Arg Leu Gln Ala Phe Ser Ser Pro Val
30 35 40 ccg gac ccg tac cgc tcg gag gat gag agc tcc gcc agg ttc gtg ccc 194
Pro Asp Pro Tyr Arg Ser Glu Asp Glu Ser Ser Ala Arg Phe Val Pro
45 50 55 60 cgc tac aat ttc acc cgc ggc gac ctc ctg cgc aag gta gac ttc gac 242
Arg Tyr Asn Phe Thr Arg Gly Asp Leu Leu Arg Lys Val Asp Phe Asp
65 70 75 atc aag ggc gat gac ctg atc gtg ttc ctg cac atc cag aag acc ggg 290
Ile Lys Gly Asp Asp Leu Ile Val Phe Leu His Ile Gln Lys Thr Gly
80 85 90 ggc acc act ttc ggc cgc cac ttg gtg cgt aac atc cag ctg gag cag 338
Gly Thr Thr Phe Gly Arg His Leu Val Arg Asn Ile Gln Leu Glu Gln
95 100 105 ccg tgc gag tgc cgc gtg ggt cag aag aaa tgc act tgc cac cgg ccg 386
Pro Cys Glu Cys Arg Val Gly Gln Lys Lys Cys Thr Cys His Arg Pro
110 115 120 ggt aag cgg gaa acc tgg ctc ttc tcc agg ttc tcc acg ggc tgg agc 434
Gly Lys Arg Glu Thr Trp Leu Phe Ser Arg Phe Ser Thr Gly Trp Ser
125 130 135 140 tgc ggg ttg cac gcc gac tgg acc gag ctc acc agc tgt gtg ccc tcc 482
Cys Gly Leu His Ala Asp Trp Thr Glu Leu Thr Ser Cys Val Pro Ser
145 150 155 gtg gtg gac ggc aag cgc gac gcc agg ctg aga ccg tcc agg tgg agg 530
Val Val Asp Gly Lys Arg Asp Ala Arg Leu Arg Pro Ser Arg Trp Arg
160 165 170 att ttt cag att cta gat gca gca agt aag gat aaa cgg ggt tct cca 578
Ile Phe Gln Ile Leu Asp Ala Ala Ser Lys Asp Lys Arg Gly Ser Pro -continued

```
      175                 180                 185

aac act aac gca ggc gcc aac tct ccg tca tcc aca aag acc cgg aac      626
Asn Thr Asn Ala Gly Ala Asn Ser Pro Ser Ser Thr Lys Thr Arg Asn
    190                 195                 200

aca tct aag agt ggg aag aac ttc cac tac atc acc atc ctc cga gac      674
Thr Ser Lys Ser Gly Lys Asn Phe His Tyr Ile Thr Ile Leu Arg Asp
205                 210                 215                 220

cca gtg tcc cgg tac ttg agt gag tgg agg cat gtc cag aga ggg gca      722
Pro Val Ser Arg Tyr Leu Ser Glu Trp Arg His Val Gln Arg Gly Ala
                225                 230                 235

aca tgg aaa gca tcc ctg cat gtc tgc gat gga agg cct cca acc tcc      770
Thr Trp Lys Ala Ser Leu His Val Cys Asp Gly Arg Pro Pro Thr Ser
            240                 245                 250

gaa gag ctg ccc agc tgc tac act ggc gat gac tgg tct ggc tgc ccc      818
Glu Glu Leu Pro Ser Cys Tyr Thr Gly Asp Asp Trp Ser Gly Cys Pro
        255                 260                 265

ctc aaa gag ttt atg gac tgt ccc tac aat cta gcc aac aac cgc cag      866
Leu Lys Glu Phe Met Asp Cys Pro Tyr Asn Leu Ala Asn Asn Arg Gln
    270                 275                 280

gtg cgc atg ctc tcc gac ctg acc ctg gta ggc tgc tac aac ctc tct      914
Val Arg Met Leu Ser Asp Leu Thr Leu Val Gly Cys Tyr Asn Leu Ser
285                 290                 295                 300

gtc atg cct gaa aag caa aga aac aag gtc ctt ctg gaa agt gcc aag      962
Val Met Pro Glu Lys Gln Arg Asn Lys Val Leu Leu Glu Ser Ala Lys
                305                 310                 315

tca aat ctg aag cac atg gcg ttc ttc ggc ctc act gag ttt cag cgg     1010
Ser Asn Leu Lys His Met Ala Phe Phe Gly Leu Thr Glu Phe Gln Arg
            320                 325                 330

aag acc caa tat ctg ttt gag aaa acc ttc aac atg aac ttt att tcg     1058
Lys Thr Gln Tyr Leu Phe Glu Lys Thr Phe Asn Met Asn Phe Ile Ser
        335                 340                 345

cca ttt acc cag tat aat acc act agg gcc tct agt gta gag atc aat     1106
Pro Phe Thr Gln Tyr Asn Thr Thr Arg Ala Ser Ser Val Glu Ile Asn
    350                 355                 360

gag gaa att caa aag cgt att gag gga ctg aat ttt ctg gat atg gag     1154
Glu Glu Ile Gln Lys Arg Ile Glu Gly Leu Asn Phe Leu Asp Met Glu
365                 370                 375                 380

ttg tac agc tat gcc aaa gac ctt ttt ttg cag agg tat cag ttt atg     1202
Leu Tyr Ser Tyr Ala Lys Asp Leu Phe Leu Gln Arg Tyr Gln Phe Met
                385                 390                 395

agg cag aaa gag cat cag gag gcc agg cga aag cgt cag gaa caa cgc     1250
Arg Gln Lys Glu His Gln Glu Ala Arg Arg Lys Arg Gln Glu Gln Arg
            400                 405                 410

aaa ttt ctg aag gga agg ctc ctt cag acc cat ttc cag agc cag ggt     1298
Lys Phe Leu Lys Gly Arg Leu Leu Gln Thr His Phe Gln Ser Gln Gly
        415                 420                 425

cag ggc cag agc cag aat ccg aat cag aat cag agt cag aac cca aat     1346
Gln Gly Gln Ser Gln Asn Pro Asn Gln Asn Gln Ser Gln Asn Pro Asn
    430                 435                 440

ccg aat gcc aat cag aac ctg act cag aat ctg atg cag aat ctg act     1394
Pro Asn Ala Asn Gln Asn Leu Thr Gln Asn Leu Met Gln Asn Leu Thr
445                 450                 455                 460

cag agt ttg agc cag aag gag aac cgg gaa agc ccg aag cag aac tca     1442
Gln Ser Leu Ser Gln Lys Glu Asn Arg Glu Ser Pro Lys Gln Asn Ser
                465                 470                 475

ggc aag gag cag aat gat aac acc agc aat ggc acc aac gac tac ata     1490
Gly Lys Glu Gln Asn Asp Asn Thr Ser Asn Gly Thr Asn Asp Tyr Ile
            480                 485                 490

ggc agt gta gag aaa tgg cgt taa                                     1514
```

-continued

```
Gly Ser Val Glu Lys Trp Arg
        495


<210> SEQ ID NO 4
<211> LENGTH: 499
<212> TYPE: PRT
<213> ORGANISM: Homo sapiens

<400> SEQUENCE: 4

Met Asp Glu Lys Ser Asn Lys Leu Leu Leu Ala Leu Val Met Leu Phe
  1               5                  10                  15

Leu Phe Ala Val Ile Val Leu Gln Tyr Val Cys Pro Gly Thr Glu Cys
             20                  25                  30

Gln Leu Leu Arg Leu Gln Ala Phe Ser Ser Pro Val Pro Asp Pro Tyr
         35                  40                  45

Arg Ser Glu Asp Glu Ser Ser Ala Arg Phe Val Pro Arg Tyr Asn Phe
     50                  55                  60

Thr Arg Gly Asp Leu Leu Arg Lys Val Asp Phe Asp Ile Lys Gly Asp
 65                  70                  75                  80

Asp Leu Ile Val Phe Leu His Ile Gln Lys Thr Gly Gly Thr Thr Phe
                 85                  90                  95

Gly Arg His Leu Val Arg Asn Ile Gln Leu Glu Gln Pro Cys Glu Cys
            100                 105                 110

Arg Val Gly Gln Lys Lys Cys Thr Cys His Arg Pro Gly Lys Arg Glu
        115                 120                 125

Thr Trp Leu Phe Ser Arg Phe Ser Thr Gly Trp Ser Cys Gly Leu His
    130                 135                 140

Ala Asp Trp Thr Glu Leu Thr Ser Cys Val Pro Ser Val Val Asp Gly
145                 150                 155                 160

Lys Arg Asp Ala Arg Leu Arg Pro Ser Arg Trp Arg Ile Phe Gln Ile
                165                 170                 175

Leu Asp Ala Ala Ser Lys Asp Lys Arg Gly Ser Pro Asn Thr Asn Ala
            180                 185                 190

Gly Ala Asn Ser Pro Ser Ser Thr Lys Thr Arg Asn Thr Ser Lys Ser
        195                 200                 205

Gly Lys Asn Phe His Tyr Ile Thr Ile Leu Arg Asp Pro Val Ser Arg
    210                 215                 220

Tyr Leu Ser Glu Trp Arg His Val Gln Arg Gly Ala Thr Trp Lys Ala
225                 230                 235                 240

Ser Leu His Val Cys Asp Gly Arg Pro Pro Thr Ser Glu Glu Leu Pro
                245                 250                 255

Ser Cys Tyr Thr Gly Asp Asp Trp Ser Gly Cys Pro Leu Lys Glu Phe
            260                 265                 270

Met Asp Cys Pro Tyr Asn Leu Ala Asn Asn Arg Gln Val Arg Met Leu
        275                 280                 285

Ser Asp Leu Thr Leu Val Gly Cys Tyr Asn Leu Ser Val Met Pro Glu
    290                 295                 300

Lys Gln Arg Asn Lys Val Leu Leu Glu Ser Ala Lys Ser Asn Leu Lys
305                 310                 315                 320

His Met Ala Phe Phe Gly Leu Thr Glu Phe Gln Arg Lys Thr Gln Tyr
                325                 330                 335

Leu Phe Glu Lys Thr Phe Asn Met Asn Phe Ile Ser Pro Phe Thr Gln
            340                 345                 350

Tyr Asn Thr Thr Arg Ala Ser Ser Val Glu Ile Asn Glu Glu Ile Gln
        355                 360                 365
```

-continued

Lys Arg Ile Glu Gly Leu Asn Phe Leu Asp Met Glu Leu Tyr Ser Tyr
370 375 380

Ala Lys Asp Leu Phe Leu Gln Arg Tyr Gln Phe Met Arg Gln Lys Glu
385 390 395 400

His Gln Glu Ala Arg Arg Lys Arg Gln Glu Gln Arg Lys Phe Leu Lys
405 410 415

Gly Arg Leu Leu Gln Thr His Phe Gln Ser Gln Gly Gln Gly Gln Ser
420 425 430

Gln Asn Pro Asn Gln Asn Gln Ser Gln Asn Pro Asn Pro Asn Ala Asn
435 440 445

Gln Asn Leu Thr Gln Asn Leu Met Gln Asn Leu Thr Gln Ser Leu Ser
450 455 460

Gln Lys Glu Asn Arg Glu Ser Pro Lys Gln Asn Ser Gly Lys Glu Gln
465 470 475 480

Asn Asp Asn Thr Ser Asn Gly Thr Asn Asp Tyr Ile Gly Ser Val Glu
485 490 495

Lys Trp Arg

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ccagcgtcgg gaacatggat 20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gccatttaac gccatttctc 20